United States Patent
Sreekrishna et al.

(10) Patent No.: US 9,427,415 B2
(45) Date of Patent: Aug. 30, 2016

(54) METHODS AND COMPOSITIONS FOR MODIFYING SENSORIAL PERCEPTION

(71) Applicant: The Procter & Gamble Company, Cincinnati, OH (US)

(72) Inventors: Koti Tatachar Sreekrishna, Mason, OH (US); Yakang Lin, Liberty Township, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

(21) Appl. No.: 14/666,394

(22) Filed: Mar. 24, 2015

(65) Prior Publication Data
US 2015/0272907 A1    Oct. 1, 2015

Related U.S. Application Data

(60) Provisional application No. 61/973,566, filed on Apr. 1, 2014.

(51) Int. Cl.
| | |
|---|---|
| *A01N 35/00* | (2006.01) |
| *A61K 31/11* | (2006.01) |
| *A61K 8/33* | (2006.01) |
| *G01N 33/50* | (2006.01) |
| *G01N 33/68* | (2006.01) |

(52) U.S. Cl.
CPC ............... *A61K 31/11* (2013.01); *A61K 8/33* (2013.01); *G01N 33/502* (2013.01); *G01N 33/5041* (2013.01); *G01N 33/6872* (2013.01); *G01N 2500/10* (2013.01)

(58) Field of Classification Search
CPC ...................................... A61K 31/11
USPC ........................................ 514/703
See application file for complete search history.

(56) References Cited

U.S. PATENT DOCUMENTS

| | | |
|---|---|---|
| 6,335,180 B1 | 1/2002 | Julius et al. |
| 6,790,629 B2 | 9/2004 | Julius et al. |
| 6,867,009 B2 | 3/2005 | Cortright et al. |
| 7,097,991 B2 | 8/2006 | Julius et al. |
| 7,186,803 B2 | 3/2007 | Dubin et al. |
| 7,465,581 B2 | 12/2008 | Bevan et al. |
| 2005/0266435 A1 | 12/2005 | Hackos et al. |
| 2006/0154886 A1 | 7/2006 | Weihe et al. |
| 2010/0278991 A1 | 11/2010 | Haught et al. |
| 2010/0316615 A1 | 12/2010 | Kurreck et al. |
| 2011/0178181 A1 | 7/2011 | Baker et al. |
| 2013/0315843 A1 | 11/2013 | Haught et al. |

FOREIGN PATENT DOCUMENTS

| | | | | |
|---|---|---|---|---|
| JP | 2011205 | * | 10/2011 | |
| WO | WO 200135768 | * | 5/2001 | ............... A23L 3/34 |
| WO | WO 2013/176897 A2 | | 11/2013 | |

OTHER PUBLICATIONS

Chambers et al. Combinatorial Chemistry & High Throughput Screening, 2003, 6, 355-362.*
Sreekrishna et al. Pulmonary Pharmacology & Therapeutics, Academic Press, GB. 2010. 24(3), p. 8.*
Fischer Pfluegers Archiv (2014), 466(12), 2229-2241.*
Zhang et al. Phytotheraphy Research, 2010, 25, 1666-167.*
International Search Report and Written Opinion for 13270M—PCT/US2015/022170 dated Jun. 16, 2015.
Mitchell, Jennifer E. et al. "Expression and characterization of the intracellular vanilloid receptor (TRPV1) in bronchi from patients with chronic cough", Experimental Lung Research, vol. 31, No. 3, Apr. 1, 2005, pp. 295-306.
Sadofsky, LR et al. "Characterisation of a HEK293 cell line permanently co-expressing the cough receptors Transient Receptor Potential Ankyrin 1 and Vanilloid 1 (TRPA1 and TRPV1)", Pulmornary Pharmacology & Therapeutics, Academic Press, GB, vol. 24, No. 3, Jun. 1, 2010, p. e8.
Sadofsky, Laura R. et al., "Unique Responses are Observed in Transient Receptor Potential Ankyrin 1 and Vanilloid 1 (TRPA1 and TRPV1) Co-Expressing Cells.", Cells 2014, vol. 3, No. 2, 2014, pp. 616-626.
Yansong, Zhang et al. "Modulation of Transient Receptor Potential (TRP) Channels by Chinese Herbal Extracts", Phytotherapy Research, vol. 25, No. 11, Mar. 23, 2011, pp. 1666-1670.

* cited by examiner

*Primary Examiner* — Nizal Chandrakumar
(74) *Attorney, Agent, or Firm* — Alexandra S. Anoff (57) ABSTRACT

Compounds and methods for modifying sensory perception associated with transient sensory receptors TRPA1, TRPV1, and TRPA1V1. A method for screening compounds for modulation of TRPA1, TRPV1, and/or TRPA1V1. Compositions comprising TRPA1V1 agonists or antagonists, for modifying sensory perception of the compositions.

1 Claim, 2 Drawing Sheets

METHODS AND COMPOSITIONS FOR MODIFYING SENSORIAL PERCEPTION

FIELD OF THE INVENTION

The invention is directed to compounds, compositions, and methods of altering sensory perception associated with TRPA1, TRPV1, or TRPA1V1 receptor activation. The invention further relates to methods for identifying and/or assessing the efficacy of agonists or antagonists of TRPA1, TRPV1 or TRPA1V1 sensory receptors.

BACKGROUND OF THE INVENTION

Transient receptor potential (TRP) ankyrin 1 (TRPA1) and vanilloid 1 (TRPV1) receptors are implicated in the modulation of cough and nociception. TRPA1 and TRPV1 have important roles in the sensation of pain, temperature, inflammation and cough in animals and man. TRPV1 is activated by warm temperatures (above 43° C.), protons and noxious chemicals such as capsaicin and resiniferatoxin. TRPA1 is activated by cold temperatures (below 17° C.), and a wide range of irritating and pain stimulating chemicals such as acrolein (found in smoke), formalin, mustard oil and allicin (found in onions and garlic) as well as cinnamaldehyde (extracted from cinnamon). Occasionally, TRPA1 and/or TRPV1 respond to compounds which are potentially beneficial, possibly creating a sense of irritation, burning, or pain that can discourage the use of beneficial products.

Functional TRP channels have been thought to be tetramers, possibly either homo-tetramers or even hetero-tetramers. In vivo, TRPA1 is known to be expressed in the same sensory neurons as TRPV1 and pharmacological interaction between the two receptors has been established. Direct interaction resulting in hetero-tetramers between these two channels has been demonstrated using transient co-expression of the two receptors in CHO cells. Nonetheless, in vitro models for irritation, burning, and pain have tended to focus on TRPA1 or TRPV1 rather than TRPA1V1.

There remains a need to modify unpleasant sensations associated with beneficial products.

SUMMARY OF THE INVENTION

In some aspects, the invention relates to a method for screening compounds for modulation of TRPA1V1 activity. The method may comprise providing a cell line stably co-expressing TRPA1 and TRPV1, wherein the cell line may comprise TRPA1V1 hetero-tetramer and at least one of TRPA1 homo-tetramer or TRPV1 homo-tetramer. The method may comprise measuring the baseline calcium ion channel activity of the cell line. The method may comprise exposing the cell line to a test composition. The method may comprise measuring the ion channel activity of the cell line after exposure to the test compound.

In some aspects, the invention relates to a method for screening compounds for modulation of TRPA1 or TRPV1 activity. The method may comprise providing a cell line stably co-expressing TRPA1 and TRPV1, wherein the cell line may comprise TRPA1V1 hetero-tetramer and at least one of TRPA1 homo-tetramer or TRPV1 homo-tetramer. The method may comprise measuring the baseline calcium ion channel activity of the cell line. The method may comprise exposing the cell line to a test composition. The method may comprise measuring the ion channel activity of the cell line after exposure to the test compound.

In some aspects, the invention relates to a method of reducing the sensory perception of burning, irritation, or pain from exposure to an oral care or topical composition. The method may comprise providing an oral care or topical composition comprising an agonist of TRPA1 and/or TRPV1. The method may comprise incorporating into the oral care or topical composition a TRPA1V1 modulator selected from the group consisting of isoamyl 3-(2-furan) propionate; ethyl 3-hydroxyoctanoate; geraniol; 5-oxodecanoic acid; vanillylacetone; isobutyl N-methyl anthranilate; 2-ethylbutyric acid; decanoic acid; p-cresol; 1-ethylhexyl tiglate; ethyl vinyl ketone; 3,7-Dimethyl-7-octen-1-ol; Octyl 2-furoate; cis-3-nonen-1-ol; piperine; gluconic acid, monopotassium salt; tartaric acid; trans,trans-2,4-undecadien-1-al; 3,5,5-Trimethylhexanal; (E)-2-Nonenal; Citronellol; 5-Phenyl-1-pentanol; 3-Methyl-5-propyl-2-cyclohexen-1-one; Benzaldehyde propylene glycol acetal; Vanillin propylene glycol acetal; Rhodinol; (E,E)-2,4-Dodecadienal; (E,E)-2,4-Decadienal; 2-Hexen-4-one; Bisabolene; 10-Undecenal; 3-Methyl-1-phenyl-3-pentanol; and combinations thereof. The TRPA1V1 modulator may be present in an amount effective to reduce the activation of TRPA1V1 relative to the activation of TRPA1 and/or TRPV1.

DETAILED DESCRIPTION OF THE INVENTION

Despite the prior observation of hetero-tetramer receptors comprising TRPA1 and TRPV1 subunits, previous efforts to study irritation potential in vitro have focused on the TRPA1 and TRPV1 receptors, without regard to the TRPA1V1 hetero-tetramers. We have found that there is value in using TRPV1 (SEQ ID NO: 1) and TRPA1 (SEQ ID NO: 2) co-expressing cells to study the irritation potential of compounds because TRPA1V1 activation is not predictable based on TRPA1 and/or TRPV1 activation. In addition to possible down-modulation of TRPA1V1 by TRPA1 or TRPV1 activators, in some cases there are synergistic increases in response across the three receptor types, and, additionally, there are compounds which can activate TRPA1V1 without activating either TRPA1 or TRPV1. This is important for the practical application of irritancy data, because TRPA1V1 activation is believed to be a better predictor of irritancy, as TRPA1V1 hetero-tetramers are more common in sensory nerves than TRPA1 or TRPV1 homo-tetramers.

TRPA1 and TRPV1 are co-expressed in many sensory cells, including in sensory cells found across the exterior of the human body, head-to-toe, and in the mucous membranes of the respiratory and gastrointestinal tracts. TRPA1 and TRPV1 are believed to be associated with irritancy triggered by a wide variety of stimuli, including food, medications, environmental conditions, illnesses, and topical treatments. In many cells where TRPA1 and TRPV1 are both expressed, TRPA1V1 hetero-tetramers are also observed.

As used herein, "isolated compound" refers to a composition that has been purified or synthesized such that a single chemical entity predominates, excluding any solvent. In contrast, a "complex extract," as used herein, refers to a composition comprising two or more chemical entities, in addition to any solvent, and may comprise dozens or hundreds of distinct chemical entities. A complex extract may be characterized by its source material and extraction process, rather than by its chemical composition.

As used herein, the terms "agonist" or "activator" refers to a composition that activates a sensory receptor. Activation of the sensory receptors TRPA1, TRPV1, and TRPA1V1 may be measured by calcium flux, as described in Example 1, or suitable alternative methods, including, without limitation, measurement of membrane potential changes, cellular calcium imaging, electrophysiological methods, or other methods for observing the activation of ion channels. An agonist or activator generates at least 20%, preferably at least 25% more receptor activity than a physiologically relevant baseline. An exemplary baseline is described in Example 1. In contrast, an "antagonist" refers to a composition that decreases the activity of a sensory receptor. An antagonist generates at least 20%, preferably at least 25% less receptor activity than a physiologically relevant baseline.

As used herein, the term "modulator" refers to a composition that can alter the activity of a sensory receptor, either by increasing or decreasing activity of the sensory receptor relative to a control condition.

All percentages and ratios used hereinafter are by weight of total composition, unless otherwise indicated. All percentages, ratios, and levels of ingredients referred to herein are based on the actual amount of the ingredient, and do not include solvents, fillers, or other materials with which the ingredient may be combined as a commercially available product, unless otherwise indicated.

All measurements referred to herein are made at 25° C. unless otherwise specified.

As used herein, the word "or" when used as a connector of two or more elements is meant to include the elements individually and in combination; for example X or Y, means X or Y or both.

By "personal care composition" is meant a product, which in the ordinary course of usage is applied to or contacted with a body surface to provide a beneficial effect. Body surface includes skin, for example dermal or mucosal; body surface also includes structures associated with the body surface for example hair, teeth, or nails. Examples of personal care compositions include a product applied to a human body for improving appearance, cleansing, and odor control or general aesthetics. Non-limiting examples of personal care compositions include hair coloring compositions, oral care compositions, after shave gels and creams, pre-shave preparations, shaving gels, creams, or foams, moisturizers and lotions, cough and cold compositions, leave-on skin lotions and creams, shampoos, conditioners, shower gels, bar soaps, toilet bars, antiperspirants, deodorants, depilatories, lipsticks, foundations, mascara, sunless tanners and sunscreen lotions.

By "oral care composition", as used herein, is meant a product, which in the ordinary course of usage, is not intentionally swallowed for purposes of systemic administration of particular therapeutic agents, but is rather retained in the oral cavity for a time sufficient to contact dental surfaces or oral tissues. Examples of oral care compositions include dentifrice, mouth rinse, mousse, foam, mouth spray, lozenge, chewable tablet, chewing gum, tooth whitening strips, floss and floss coatings, breath freshening dissolvable strips, or denture care or adhesive product. The oral care composition may also be incorporated onto strips or films for direct application or attachment to oral surfaces.

The term "dentifrice", as used herein, includes tooth or subgingival-paste, gel, or liquid formulations unless otherwise specified. The dentifrice composition may be a single phase composition or may be a combination of two or more separate dentifrice compositions. The dentifrice composition may be in any desired form, such as deep striped, surface striped, multilayered, having a gel surrounding a paste, or any combination thereof. Each dentifrice composition in a dentifrice comprising two or more separate dentifrice compositions may be contained in a physically separated compartment of a dispenser and dispensed side-by-side.

As used herein, the term "topical", in reference to a composition, includes any composition intended to be applied to the skin, including the scalp, hair, or nails. Exemplary topical compositions include lotions; moisturizers; sunscreens; perfumes; color cosmetics, such as blush, foundation, or eye shadow; hair treatments, including hair dyes, shampoos, conditioners, texture modifiers such as relaxers, curling products, and treatments to increase volume or shine, and styling aids, such as hair gel and hairspray; nail polish or nail strengtheners; cuticle oil; soaps, detergents, and body washes; compositions for shaving, including shave gels or foams and after-shave treatments; toners; and medicaments.

A "medicament", as used herein, is any agent that promotes recovery from injury or illness, inclusive of pain relievers.

As used herein, "toxic" refers to a composition or substance capable of damaging tissues under relevant conditions of exposure, including duration of exposure, nature of exposure (e.g., respiratory, ingestion), and concentration of the composition or substance.

As used herein, "gastrointestinal symptoms" refers to undesired gastrointestinal events, including bloating, cramping, vomiting, diarrhea, excessive gas production, with or without associated tissue damage.

As used herein, "stably co-expressing" refers to a cell line which produces a consistent, reproducible response to known agonists of TRPV1 (capsaicin or suitable alternative) and TRPA1 (allylisothiocyanate or suitable alternative).

As used herein, the term "irritation", "burning", and "pain" refer to undesirable sensory perceptions, noticeable to a human subject able to report them or measurable by ion channel activation or comparable analytical methodology. These sensations are associated with, among other receptors, TRPA1 and TRPV1. The words irritation, burning, and pain may variously be used by human subjects to describe their perception of stimuli which are known to activate TRPA1 and/or TRPV1.

Irritation, burning, and pain may be associated with stimuli which are, at least in the short-term or at low concentrations, safe. As an example, a hot surface may create a sensation of burning or pain significant enough to trigger an involuntary movement of the body away from the hot surface, even if the surface is not, in fact, hot enough to cause tissue damage from indirect or very brief contact. If the stimulus has benefits, such as cosmetic or medical benefits, it may be desirable to reduce or entirely override the perception of irritancy, burning, or pain associated with the stimulus.

In some aspects, the invention relates to a method of reducing the sensory perception of burning, irritation, or pain from exposure to an oral care or topical composition. The method may comprise providing an oral care or topical composition comprising an agonist of TRPA1 and/or TRPV1. The method may comprise incorporating into the oral care or topical composition a TRPA1V1 modulator, particularly a modulator which decreases the measurable activity of TRPA1V1. The TRPA1V1 modulator may be selected from the group consisting of isoamyl 3-(2-furan) propionate; ethyl 3-hydroxyoctanoate; geraniol; 5-oxodecanoic acid; vanillylacetone; isobutyl N-methyl anthranilate; 2-ethylbutyric acid; decanoic acid; p-cresol; 1-ethylhexyl tiglate; ethyl vinyl ketone; 3,7-Dimethyl-7-octen-1-ol; Octyl 2-furoate; cis-3-nonen-1-ol; piperine; gluconic acid, monopotassium salt; tartaric acid; trans,trans-2,4-undecadien-1-al; 3,5,5-Trimethylhexanal; (E)-2-Nonenal; Citronellol; 5-Phenyl-1-pentanol; 3-Methyl-5-propyl-2-cyclohexen-1-one; Benzaldehyde propylene glycol acetal; Vanillin propylene glycol acetal; Rhodinol; (E,E)-2,4-Dodecadienal; (E,E)-2,4-Decadienal; 2-Hexen-4-one; Bisabolene; 10-Undecenal; 3-Methyl-1-phenyl-3-pentanol; and combinations thereof. The TRPA1V1 modulator may be present in the composition in an amount effective to reduce the activation of TRPA1V1 relative to the activation of TRPA1 and/or TRPV1. The TRPA1V1 modulator may be trans,trans-2,4-undecadien-1-al.

The method may be used with oral compositions which are ingestible or non-ingestible. Oral compositions of interest may include rinses, foods, beverages, medicaments, dentifrices, and the like. The method may be used with topical compositions. Exemplary topical compositions include moisturizers; medicaments; toners; depilatories; color cosmetics; compositions intended to treat the hair or scalp, including shampoos, conditioners, hair dyes, styling aids, and/or texture modifiers; and combinations thereof. In any of these exemplary compositions, the TRPA1V1 modulator may be trans,trans-2,4-undecadien-1-al.

In some aspects, the invention relates to a method for isolating trigeminal response in a subject. The method may comprise exposing the subject to a TRPA1 activator that does not modulate TRPV1 or TRPA1V1. The method may comprise exposing the subject to a TRPV1 activator that does not modulate TRPA1 or TRPA1V1 activity. The method may comprise exposing the subject to a TRPA1V1 activator that does not modulate TRPA1 or TRPV1 activity. By comparing the responses to the TRPA1, TRPV1, and TRPA1V1 activators, it is possible to isolate the trigeminal response. By studying the trigeminal effect of individual compounds known to specifically activate only one of the TRPA1, TRPV1, and TRPA1V1 receptors, it is possible to isolate the trigeminal response specific to each of those receptors.

An exemplary TRPA1 activator which does not modulate TRPV1 or TRPA1V1 is propylparaben. Suitable TRPV1 activators which do not modulate TRPA1 or TRPA1V1 include, without limitation, 2,4,5-trimethyl-3-oxazoline; heptaldehyde; 2-ethylfuran; desoxycholic acid; malic acid; 2-methylbutyl isovalerate, and combinations thereof.

Just as irritation, burning, and pain may be associated with stimuli which are safe, some stimuli which are dangerous may not be associated with irritation, burning, or pain. Exemplary compositions which may be useful but dangerous to ingest or touch with bare skin include many household cleaners, or topical medicaments that are not suitable for ingestion. If a composition is dangerous if touched or ingested, it may be desirable to increase the perception of irritancy, burning, or pain associated with touching or ingesting the composition.

In some aspects, the invention relates to a method for increasing the perception of burning, irritation, or pain associated with topical exposure to a composition. The method may comprise providing a composition for which it is desired to discourage contact between the composition and the skin or scalp, and incorporating into the composition a TRPA1V1 activator. The TRPA1V1 activator may also activate TRPA1 or TRPV1. The TRPA1V1 activator may also activate TRPA1 and TRPV1. The composition may be toxic. The composition may cause undesirable cosmetic changes in the skin, such as discoloration. It is not necessary that the composition provide a noticeable perception of burning, irritation, or pain without the addition of the TRPA1V1 activator, although, in some cases, the composition will provoke some discomfort which is intensified by the addition of the TRPA1V1 activator.

In some aspects, the invention relates to a method for increasing the perception of burning, irritation, or pain associated with oral exposure to a composition. The method may comprise providing a composition for which it is desired to discourage contact between the composition and the mouth, mucous membranes, or digestive tract, and incorporating into the composition a TRPA1V1 activator. The TRPA1V1 activator may also activate TRPA1 or TRPV1. The TRPA1V1 activator may also activate TRPA1 and TRPV1. The composition may be toxic. The composition may cause gastrointestinal symptoms if ingested. It is not necessary that the composition provide a noticeable perception of burning, irritation, or pain without the addition of the TRPA1V1 activator, although, in some cases, the composition will provoke some discomfort which is intensified by the addition of the TRPA1V1 activator.

In some aspects, the invention relates to a composition comprising a TRPA1V1 antagonist. The composition may be an oral care or topical composition. The composition may comprise an agonist of TRPA1 and/or TRPV1. Counter intuitively, the TRPA1V1 antagonist may help reduce the perception of irritation, burning, or pain from oral care or topical contact with the composition, even if the particular antagonist used is an agonist for TRPA1 and/or TRPV1. In some aspects, the invention relates to a composition comprising a TRPA1 agonist that down-modulates TRPV1 activity. In some aspects, the invention relates to a composition comprising a TRPV1 agonist that down-modulates TRPA1 activity.

In some aspects, the invention relates to a composition comprising a TRPA1V1 agonist. The composition may be an oral care or topical composition. The composition may be toxic, or may cause undesirable cosmetic changes in the skin, or may cause gastrointestinal symptoms if ingested. The composition may comprise an antagonist of TRPA1 and/or TRPV1. Counter intuitively, the TRPA1V1 agonist may increase the perception of irritation, burning, or pain from oral care or topical contact with the composition (thereby discouraging prolonged contact or ingestion), even if the particular agonist used is an antagonist for TRPA1 and/or TRPV1. In some aspects, the invention relates to a composition comprising a TRPA1 antagonist that activates TRPV1. In some aspects, the invention relates to a composition comprising a TRPV1 agonist that activates TRPA1.

In some aspects, the invention relates to a method for screening compounds for modulation of TRPA1 activity. The method may comprise providing cell lines stably co-expressing TRPA1, TRPV1, and/or TRPA1V1. The method may comprise measuring the baseline ion channel activity of the cell line. The baseline ion channel activity is measured prior to exposure to any control substance (e.g., known modulator with predictable effect) or test composition. With respect to TRPA1, TRPV1, and TRPA1V1, ion channel activity may be measured as calcium flux across a cell membrane. Suitable alternatives to calcium flux measurements include measurement of membrane potential changes, cellular calcium imaging, electrophysiological methods, and other methods of observing ion channel activation. The measurement of calcium flux is well known and can be used with commercially available test kits, such as the kit described in Example 1. TRPA1 activity can be distinguished from TRPV1 and TRPA1V1 activity as known in the art. As an example, by using a cell expressing only TRPA1 or TRPV1, it is possible to screen for compounds that activate specifically TRPA1 or TRPV1.

The method may comprise exposing the cell line to a test composition. The test composition may be a substance with unknown effect (if any) on the receptor of interest. The test composition may be added to the cell culture in concentrations ranging in molarity from 200 nM to 5 mM, more preferably from 350 nM to 1 mM, more preferably from 100 µM to 1 mM. If the test composition is a complex extract or for any other reason cannot be conveniently measured by molarity, the test composition may be added to the cell culture in concentrations ranging from 0.0002% to 0.008%. It should be understood that the test composition will be further diluted upon addition to the cell culture. The exemplary ranges provided are suggested for a 100 µL aliquot of cell line suspended in assay reagent. Significantly larger or smaller cell line aliquots may require different test composition concentrations. The cell line may be incubated with the test composition. The cell line may be incubated with the test composition for 15-60 minutes, more preferably, 20-40 minutes. The method may comprise measuring the ion channel activity of the cell line after exposure to (or incubation with) the test compound.

Screening compounds for modulation of TRPA1 activity using a cell line stably co-expressing TRPA1, TRPV1, and TRPA1V1 may be beneficial in identifying previously unappreciated interactions between these receptors and/or their agonists. Similar benefits may be obtained by screening compounds for modulation of TRPV1 or TRPA1V1 activity using cell lines stably co-expressing TRPA1, TRPV1, and/or TRPA1V1.

Figure 1A:
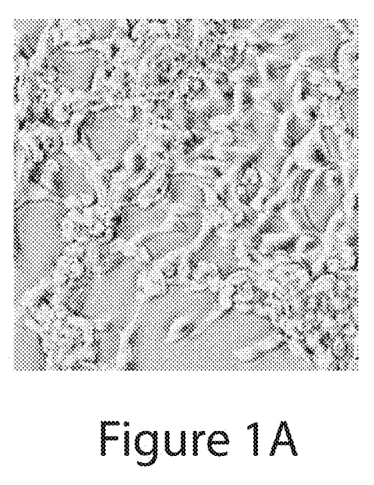
FIGS. 1A and 1B illustrates the appearance of cell cultures associated with Example 1.
Figure 1B:
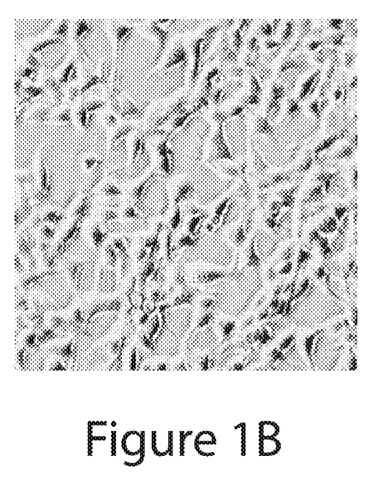

It is possible to compare the measured response to a test composition to published, predicted, or previously obtained data. In TRPV1-expressing cells, exposure to heat in excess of 30° C. may increase the basal activity of TRPV1, and may also be associated with cell clumping and other signs of poor cell health. FIG. 1A shows TRPV1-expressing cells incubated at 37° C. FIG. 1B shows TRPV1-expressing cells incubated at 25° C. Some agonists, such as capsaicin, may further exacerbate the tendency for cells to clump at high temperature. Thus, it may be desirable to pre-incubate TRPV1-expressing cells at a temperature between 22° C. and 30° C. prior to exposing the cell line to a control agonist and/or test composition. The cell line may be pre-incubated between 22° C. and 30° C. for 15-60 minutes prior to exposing the cell line to the control agonist and/or test composition, more preferably for 20-40 minutes.

It is possible to distinguish the ion channel activation associated with one receptor versus another receptor or receptors even in cell lines expressing two or more related receptors using methods known in the art. For example, a parallel screening for activation of related ion channels can be used to eliminate positive activation results for compounds that activate multiple types of ion channels. Another exemplary method is to test a compound which appears to be an agonist for a specific receptor in the presence of a known antagonist for that specific receptor, to check for a reduction in response. More details about an exemplary methodology are included in Zhang, Y.; Sreekrishna, K.; Lin, Y.; Huang, L.; Eickhoff, D.; Degenhardt, D.; Xu T. Modulation of Transient Receptor Potential (TRP) Channels by Chinese Herbal Extracts. *Phytother. Res.* 2011, 25, 1666-1670.

Example 1

Materials

Allyl isothiocyanate (AITC), cinnamaldehyde, capsaicin, and calcium ionophores (A23187 and ionomycin) were obtained from Sigma Aldrich (St Louis, Mo.). All buffers, expression vectors, antibiotics, calcium dyes (Fluo-3 AM and Fluo-4 AM), and other reagents used were obtained from Life Technologies (Carlsbad, Calif.). GRAS compound library was procured from Evotec (San Francisco, Calif.).

TRPV1, TRPA1, TRPA1V1 and pcDNA3 Control Cells

Cells stably expressing human TRPV1 (sequence used is shown in SEQ ID NO: 1), human TRPA1 (sequence used is shown in SEQ ID NO: 2), as well as cells that co-express both receptors (TRPA1V1) and control (pcDNA3) cells have been described previously. Sadofsky, L. R.; Campi, B.; Trevisani, M.; Compton, S. J.; Morice, A. H. Transient receptor potential vanilloid-1-mediated calcium responses are inhibited by the alkylamine antihistamines dexbrompheniramine and chlorpheniramine. *Exp Lung Res.* 2008, 34, 681-693. Mitchell, J. E.; Campbell, A. P.; New, N. E.; Sadofsky, L. R.; Kastelik, J. A.; Mulrennan, S. A.; Compton, S. J.; Morice, A. H. Expression and characterization of the intracellular vanilloid receptor (TRPV1) in bronchi from patients with chronic cough. *Exp Lung Res.* 2005, 31, 295-306. Sadofsky, L. R.; Sreekrishna, K.; Morice, A. H Characterisation of a HEK293 cell line permanently co-expressing the cough receptors Transient Receptor Potential Ankyrin 1 and Vanilloid 1 (TRPA1 and TRPV1). The Sixth London International Symposium on Cough: A translational approach, London 24-26 Jun. 2010 (Chung, K. F.; Widdicombe, J) [Abstracts/Pulmonary Pharmacology and Therapeutics 2011, 24, e8].

Measurement of Intracellular Calcium for Activation of TRA1V1, TRPA1 and TRPV1 Cells by GRAS Compounds TRPV1, TRPA1, TRPA1V1 and pcDNA3 cells were grown in 15 mL growth medium [high glucose DMEM (Dulbecco's modification of Eagle's medium) supplemented with 10% FBS (fetal bovine serum), 100 µg/mL penicillin/streptomycin, 100 µg/mL G418] in a 75 $cm^2$ flask for 3 days in a mammalian cell culture incubator at 33° C. and 5% $CO_2$. TRP Cells were detached with 8 mL of PBS (without calcium or magnesium); for pcDNA3 cells, trypsin was used for releasing the cells. The detached cells were spun at low speed (800-900 rpm for 3 min) to pellet the cells. The PBS medium was gently removed, and the cell pellet was re-suspended in 1 mL growth medium; 12.5 µg of Fluo-4 AM calcium dye dissolved in 5 µL Pluronic F-127 (20% solution in DMSO), was added and incubated for 30 min with gentle shaking at room temperature. The cells were washed once with 45 mL assay buffer (1×HBSS, 20 mM HEPES) by low speed centrifugation (800-900 rpm for 3 min) and resuspended in 11 mL of the assay buffer in a reagent reservoir. Aliquots of 100 µL (approximately $5 \times 10^4$ cells) were dispensed in each well of the 96-well plate (BD Falcon microtest assay plate #353948). The plates were set at room temperature for 30 min. The plates were read in a FLIPR$^{TETRA}$ instrument (Molecular Devices, Sunnyvale, Calif.) at $\lambda_{ex}$ 488 nm and $\lambda_{em}$ 514 nm to record baseline fluorescence following which 20 µL of test material at 1 mM or 100 µM final concentration for pure compounds in a GRAS library or 0.004% for extracts. For agonists, capsaicin 350 nM and AITC at 30 µM; and for controls, ionomycin 10 µM and buffer alone) was added to each well using the dispenser provided in the FLIPR. The data point was recorded every 2 seconds for a total of 10 min. Data were analyzed after baseline subtraction as described previously in Smart, et al. Characterization using FLIPR of human vanilloid VR1 receptor pharmacology. *Eur J Pharmacol* 2001, 417, 51-58, and Zhang, et al. Modulation of Transient Receptor Potential (TRP) Channels by Chinese Herbal Extracts. *Phytother. Res.* 2011, 25, 1666-1670.

Activation of TRPA1V1, TRPA1 and TRPV1 Cells by GRAS Library Compounds

Figure 2:
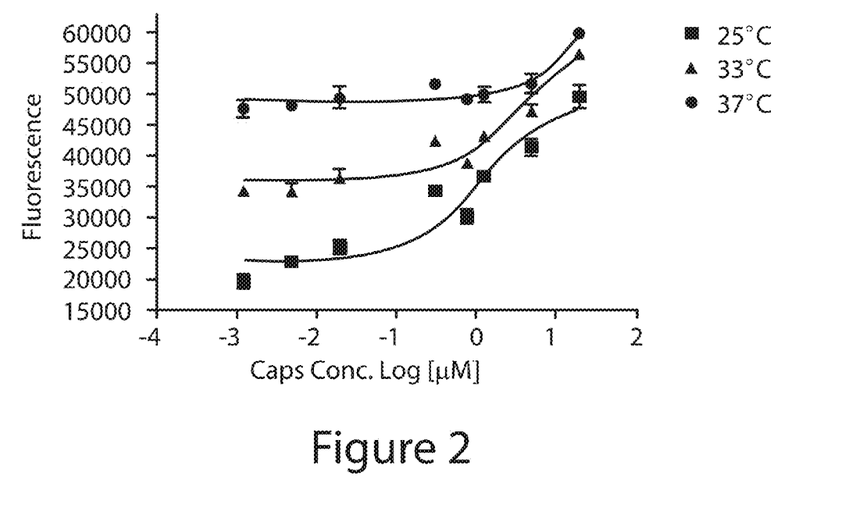
FIG. 2 is a graph showing fluorescence of cells under different growth conditions, as described in Example 1.

We observed that during cultivation of cells for several passages, TRPV1 cells cultivated at 37° C. tended to form clumps and were unhealthy presumably due to high basal activity of TRPV1 (FIG. 1A), whereas cells grown at 25° C. did not form clumps and looked healthy (FIG. 1B). Pre-incubation of cells at 25° C. for 30 minutes prior to addition of capsaicin gave superior response as compared to cells pre-incubated at 33° C. or 37° C. (FIG. 2). Cells pre-incubated at higher temperatures had proportionally higher basal activity. Thus for screening compounds we implemented the 33° C. growth temperature and 25° C. pre-incubation conditions for all three cell lines.

Agonist Hits Identified in the GRAS Compound Library Screen

Compounds that gave at least 20-25% of activity relative to benchmark agonist against at least any one of A1, V1 or A1V1 were considered an agonist. In all we identified 329 agonists out of 1620 compounds screened at 1 mM or 100 µM final dose for pure compounds or 0.004% or 0.0004% final concentration for extracts. Of these agonists 67 activated all three receptors and in 41 instances, A1 or V1 had no obvious effect on A1V1 activity. By this we mean that an A1 agonist gave similar A1V1 response (Table 1a). Whereas in other 26 other instances, A1 and/or V1 impacted A1V1 response as noted in Table 1b. We found 137 compounds that activated A1 and A1V1, but not V1 and had same or very similar level of activity of both A1 and A1V1 (Table 1c), suggesting very little or no impact of V1 on A1V1 activity in the majority of instances. However, in 39 instances, V1 caused negative modulation of A1V1 activity (Table 1d), whereas in 34 instances, V1 caused positive modulation of A1V1 response (Table 1e). We also found 12 compounds that activated V1 and A1V1, but not A1 where V1 and A1V1 activities were comparable (Table 1f), suggesting that A1 did not influence A1V1 activity in those cases. In 20 instances A1 enhanced A1V1 response (Table 1g), whereas in 12 instances, A1 negatively impacted A1V1 response (Table 1h). Interestingly, 6 compounds activated only V1, one activated only A1, and one compound activated both A1 and V1 but not A1V1 (Table 1i). These results suggest that, although in majority of instances A1V1 response correlates with A1 or V1 response, nevertheless in a significant number of instances, the activity of A1V1 is modulated, positively or negatively, by A1 or V1 in a compound specific manner.

Table 1

Summary of GRAS compound library screen for activation of TRPA1, TRPA1V1 and TRPV1 cells. Average value for activation from three independent assay plates are presented as % of agonist value (AITC, 30 µM for TRPA1 and capsaicin, 350 nM for TRPV1. For TRPA1V1, we used AITC, 30 µM or capsaicin, 350 nM depending on if the compound is an A1 agonist or a V1 agonist. For compounds that activated both A1 and V1, we used AITC for normalization). Variation among triplicates was within 10% of each other. Assayed at 1 mM for pure compounds and 0.004% for extracts.

TABLE 1(a)

Compounds that activated all three receptors, with no apparent effect of V1 on A1V1.

| GRAS Compound at 1 mM or 100 µM (*) | A1 | A1V1 | V1 |
| --- | --- | --- | --- |
| Allyl-trisulfide | 83.45 | 89.08 | 32.85 |
| Perillyl alcohol | 82.00 | 73.28 | 20.37 |
| Phenylpyruvic acid | 68.03 | 74.05 | 32.49 |
| Trans-2-Octen-1-ol | 118.4 | 103.2 | 25.98 |
| Ethyl 2-hydroxy-3-phenylpropanoate | 95.60 | 90.76 | 29.18 |
| Geranyl butyrate | 76.94 | 76.26 | 28.86 |
| Retinol palmitate | 76.39 | 76.97 | 32.78 |
| 2-Butylfuran | 68.54 | 62.77 | 20.19 |
| Alpha-Amylcinnamyl alcohol | 96.36 | 77.36 | 21.12 |
| Pseudoionone | 105.5 | 127.2 | 20.76 |
| 5-Octen-1-ol, (Z) | 62.30 | 69.24 | 20.50 |
| Helional | 78.00 | 71.85 | 23.38 |
| 2-Methoxy-4-vinylphenol | 74.81 | 81.90 | 20.66 |
| 2-(3-Phenylpropyl)pyridine | 75.97 | 74.53 | 21.47 |
| Farnesal | 97.58 | 104.4 | 41.22 |
| Beta-Cyclohomocitral | 81.44 | 66.79 | 61.74 |
| Saccharin | 92.58 | 93.25 | 80.76 |
| 3-Methyl-2-Phenylbutyraldehyde | 90.56 | 93.08 | 75.80 |
| Gamma-Nonalactone | 33.32 | 69.15 | 66.34 |
| Vanillyl ethyl ether | 38.00 | 59.64 | 67.57 |
| Cyclohexaneacetic acid | 20.60 | 61.28 | 56.63 |
| Methyl linolenate | 108 | 104 | 31 |
| Pyruvic caid cis-3-hexen-1-yl ester | 45 | 40 | 21 |
| 4-Hydroxy-5-methyl-3-furanone | 58 | 38 | 40.5 |
| 3-Octen-2-one | 52.67 | 45.60 | 30.02 |
| 4-Hydroxybenzaldehyde* | 80.4 | 163.2 | 123.1 |
| Phloretin* | 160.2 | 174.3 | 122.4 |
| 2-Napthlaenthiol* | 66.3 | 85.2 | 120.3 |
| 2-Furfurylthio-3-methylpyrazine* | 80.7 | 80.9 | 31.3 |
| Benzothiazole* | 51.3 | 74.4 | 33.4 |
| Propyl 2-methyl-3-furyl disulfide | 210.3 | 194.3 | 25 |
| 2,3,6-Trimethylphenol | 90 | 91.4 | 74.8 |
| o-Eugenol | 128.4 | 158.3 | 64.5 |
| 2-Propylphenol | 126.4 | 183.8 | 96.9 |
| Isothiocyanic acid, benzyl ester | 110.3 | 180.5 | 59.2 |
| 3-Mercapto-2-pentanone | 92 | 72.6 | 59.2 |
| Linoleic acid | 169.7 | 170.4 | 24.9 |
| 1-Octen-3-one | 118 | 98.9 | 63.2 |
| 1-Phenyl-1,2-propanedione | 98.6 | 105.5 | 66.6 |
| Butylparaben | 104.7 | 98.1 | 79.1 |
| 2-Benzofurancarboxaldehyde | 91 | 102.3 | 57.6 |

TABLE 1(b)

Compounds that activated all three receptors, with A1 and/or V1 having effect on A1V1.

| GRAS Compound at 1 mM or 100 µM (*) | A1 | A1V1 | V1 | Remarks |
| --- | --- | --- | --- | --- |
| Isoamyl 3-(2-furan)propionate | 123.3 | 106.9 | 32.66 | Negative effect of V1 |
| Ethyl 3-hydroxyoctanoate | 97.29 | 76.90 | 28.05 | Negative effect of V1 |
| Geraniol | 82.52 | 63.93 | 42.16 | Negative effect of V1 |
| Thymol | 159 | 105.7 | 105.8 | Negative effect of V1 |
| (E)-2-Nonenal | 130 | 61.8 | 89 | Negative effect of V1 |
| 5-Oxodecanoic acid | 28.57 | 39.34 | 53.38 | Negative effect of A1 |
| Vanillylacetone | 22.26 | 37.75 | 60.05 | Negative effect of A1 |
| 3,5,5-Trimethylhexanal | 133 | 114.7 | 217.2 | Negative effect of A1 |

TABLE 1(b)-continued

Compounds that activated all three receptors, with A1 and/or V1 having effect on A1V1.

| GRAS Compound at 1 mM or 100 μM (*) | A1 | A1V1 | V1 | Remarks |
|---|---|---|---|---|
| Trans,trans-2,4-undecadien-1-al* | 74 | 38.4 | 87.5 | A1 and V1 have negative effect |
| Citronellol | 102 | 34.4 | 106 | A1 and V1 have negative effect |
| 5-Phenyl-1-pentanol | 119 | 52.1 | 113.1 | A1 and V1 have negative effect |
| 3-Phenylpropanol | 51.43 | 64.94 | 32.05 | A1 and V1 have a positive effect |
| 3-Methyl-5-propyl-2-cyclohexen-1-one | 69.00 | 101.0 | 59.22 | A1 and V1 have a positive effect |
| Benzaldehyde propylene glycol acetal | 48.03 | 78.33 | 34.38 | A1 and V1 additive |
| Vanillin propylene glycol acetal | 76.21 | 94.49 | 57.97 | A1 and V1 additive |
| Piperonyl isobutyrate | 61.03 | 82.33 | 30.00 | A1 and V1 additive |
| 4-Phenyl-2-butanol | 58.83 | 81.29 | 37.89 | A1 and V1 additive |
| Methyl cyclohexane-carboxylate | 45.50 | 85.17 | 69.51 | A1 and V1 additive |
| Piperitone | 90.06 | 109.1 | 53.30 | A1 and V1 additive |
| Hedione | 43.54 | 60.64 | 25.60 | A1 and V1 additive |
| Piperonyl acetate | 62.67 | 78.00 | 20.92 | A1 and V1 additive |
| Curcumin | 95.3 | 171.6 | 43.2 | A1 and V1 have a positive effect |
| 2-Cyclopentylcyclopentanone | 25 | 90.8 | 24 | A1 and V1 have a positive effect |
| Citral diethyl acetal | 53 | 130.7 | 72 | A1 and V1 have a positive effect |
| 3-Mercaptobutanone | 50.4 | 80.9 | 63.8 | A1 and V1 have a positive effect |
| Carvacrol | 115 | 134.1 | 84.6 | A1 and V1 have a positive effect |

TABLE 1(c)

Compounds that activate A1 and A1V1 with similar level of Activation of A1 and A1V1.

| GRAS Compound at 1 mM or 100 μM (*) or at 0.004% for extract (**) | A1 | A1V1 |
|---|---|---|
| 2,4-Hexadienyl propionate | 93.17 | 91.20 |
| Methyl o-formamidobenzoate | 75.42 | 75.64 |
| (E,E)-2,6-Nonadienal | 87.10 | 89.61 |
| 2-Furanmethanol, 5-methyl- | 77.31 | 76.02 |
| 2,4-Hexadienol | 78.00 | 78.68 |
| Dihydro-beta-ionone | 64.4 | 64.07 |
| Isoeugenyl phenylacetate | 59.08 | 58.40 |
| Gum benzoin, Siam** | 47.32 | 46.64 |
| Rhodinyl acetate | 89.06 | 89.69 |
| Sandalwood oil** | 92.67 | 94.94 |
| Trivertal | 35.43 | 36.46 |
| 3-Methyl-2-cyclohexen-1-one | 94.48 | 94.76 |
| Benzenemethanol | 79.64 | 78.47 |
| (+/−)-Alpha-Ionone | 64.62 | 64.21 |
| Amyl furoate | 81.09 | 87.70 |
| p-Hydroxyacetophenone | 52.82 | 49.38 |
| Methyl p-anisate | 57.47 | 66.24 |
| Ammonium carbonate | 52.81 | 58.42 |
| O-Tolyl isobutyrate | 49.37 | 57.76 |
| Allyl anthranilate | 73.80 | 75.03 |
| 2-Octenoic acid | 55.93 | 61.77 |
| Methylparaben | 62.00 | 66.33 |
| Methyl dihydrojasmonate | 54.44 | 59.58 |
| Methyl sorbate | 76.00 | 81.15 |
| Sucrose | 84.13 | 80.86 |

TABLE 1(c)-continued

Compounds that activate A1 and A1V1 with similar level of Activation of A1 and A1V1.

| GRAS Compound at 1 mM or 100 μM (*) or at 0.004% for extract (**) | A1 | A1V1 |
|---|---|---|
| Methyl 2-methoxybenzoate | 71.2 | 74.68 |
| Eugenyl acetate | 75.4 | 83.94 |
| Veratraldehyde | 73.8 | 69.76 |
| Allyl phenylacetate | 86.2 | 84.14 |
| 2-trans-6-cis-Nonadienal | 77.3 | 81.22 |
| 4-Methoxybenzylacetone | 62.3 | 71.16 |
| Methyl N-methylanthranilate | 83.62 | 86.81 |
| Cinnamyl acetate | 84.99 | 89.73 |
| N,N-Dimethylanthranilic acid methyl ester | 74.23 | 77.15 |
| Valencene | 61.97 | 66.32 |
| Ethyl vanillin propylene glycol acetal | 66.41 | 72.64 |
| Rhodinyl isovalerate | 54.92 | 48.29 |
| Saffron extract (**) | 86.70 | 92.32 |
| Chicory extract (**) | 40.72 | 45.18 |
| L-Ascorbic acid, calcium salt (2:1) | 88.00 | 93.20 |
| Maltol propionate | 85.04 | 81.97 |
| Carmine | 66.21 | 61.54 |
| (−)-Carvyl acetate | 31.2 | 37 |
| Basil oil (**) | 73.84 | 67.89 |
| Geranium oil | 71.89 | 76.78 |
| 1-Methylpyrrole-2-carboxaldehyde | 81.09 | 87.70 |
| 1-Cyclohexene-1-carboxaldehyde | 45.88 | 48.37 |
| Eugenol | 79.00 | 91.29 |
| 3-Butylidenephthalide | 119.3 | 115.4 |
| (E,E)-2,4-Hexadienal | 92.00 | 108.71 |
| Bisabolol | 68.05 | 73.53 |
| Decanoic acid | 65.12 | 73.45 |
| 2-Acetylnaphthalene | 60.28 | 69.41 |
| Isoamyl acetate | 49.63 | 61.80 |
| 4-Pentenal | 75.4 | 84.24 |
| Rhodinyl propionate | 75.56 | 86.44 |
| Isoeugenyl acetate | 57.6 | 68.34 |
| (−)-Alpha-Bisabolol | 71.26 | 83.53 |
| Phenoxyethyl propionate | 65.55 | 79.34 |
| DL-Menthol | 54.02 | 43.05 |
| Trans-2-Pentenal | 80.86 | 68.62 |
| O-Methylbenzyl acetate | 87.22 | 77.24 |
| Retinol | 80.00 | 67.79 |
| Phenethyl isothiocyanate | 92.00 | 81.46 |
| 2,6-Nonadiene, 1,1-diethoxy-, (E,Z)- | 89.30 | 74.31 |
| Alpha-Isobutylphenethyl alcohol | 73.00 | 58.62 |
| Phenethyl isothiocyanate | 92.32 | 81.46 |
| O-Methoxycinnamaldehyde | 65.3 | 55.99 |
| Methyl 4-phenylbutyrate | 58.39 | 50.30 |
| 2-Chloroacetophenone* | 93.6 | 88.8 |
| Erucin* | 74.2 | 78.9 |
| Ethyl 2-mercaptopropionate* | 88.3 | 70.2 |
| Isothiocyanic acid 4-penten-1-yl ester* | 51.6 | 47.3 |
| 3-(2-Furfuryl)-2-phenylpropenol* | 81.3 | 72.4 |
| 1,2-Propanedithiol* | 65.8 | 65.4 |
| Citronellyl butyrate* | 44.9 | 57.9 |
| Skatole* | 66.2 | 71.4 |
| Linalyl benzoate* | 44.4 | 55.3 |
| 2,5-dimethyl-1,4-dithiane-2,5-diol* | 77.5 | 87.2 |
| Citronellyl propionate* | 52.5 | 43.2 |
| 2-Methylundecanal* | 54.9 | 57.3 |
| Trans-2-dodecenal* | 79.1 | 66 |
| 3-Mercapto-2-Pentanone* | 103.4 | 100 |
| Skatole | 116.3 | 102.9 |
| 2,4-Octadienal | 80.9 | 82.7 |
| Methyl 2-methyl-3-furyl disulfide | 52.6 | 52 |
| 3-Thiazoline, 4,5-dimethyl-2-isobutyl- | 142.4 | 138.7 |
| Benzoylanthranilic acid | 145.9 | 125.6 |
| cis-3-Hexenyl cis-3-hexenoate | 106.6 | 97.4 |
| 2-Furylacetone | 60.8 | 59.5 |
| Citral | 145.4 | 132.7 |
| Cinnamyl alcohol | 89.8 | 79.4 |
| 2-Furoic acid, phenethyl ester | 155 | 145 |
| Benzyl propionate | 103.4 | 90.7 |
| 2-Phenylpropionaldehyde | 105.1 | 106.9 |
| 3-(Methylthio)hexyl acetate | 97.9 | 87.6 |
| 2-Tridecenal | 119 | 102 |
| trans-2-Octanal | 112 | 115 |
| Theaspirane | 99 | 84 |

TABLE 1(c)-continued

Compounds that activate A1 and A1V1 with similar level of Activation of A1 and A1V1.

| GRAS Compound at 1 mM or 100 µM (*) or at 0.004% for extract (**) | A1 | A1V1 |
|---|---|---|
| Anisyl formate | 89.5 | 78.2 |
| 3-mercaptopropanoate | 42.7 | 41.8 |
| Propyl 2-methyl-3-furyl disulfide | 265.7 | 242.5 |
| 2,4-Dimethylbenzaldehyde | 106.8 | 102.8 |
| 1,6-Hexanedithiol | 68.6 | 54 |
| 1,2-Propanedithiol | 66 | 73.3 |
| Nonyl alcohol | 71.1 | 69.4 |
| (E)-2-Heptenal | 112.4 | 96.6 |
| Cinnamic acid | 37.7 | 42.5 |
| Myrtenal | 95.8 | 111.3 |
| Ethyl p-anisate | 91.2 | 93.1 |
| cis-6-Nonenal | 108 | 93 |
| 4-Hydroxybenzaldehyde | 63 | 60.3 |
| L-Perillaldehyde | 127.7 | 138.2 |
| alpha-Terpinyl formate | 82.2 | 71 |
| (E,E)-Hepta-2,4-dien-1-ol | 145.6 | 133.3 |
| 2-Hexanoylfuran | 118 | 109 |
| Ethyl benzoate | 70 | 60 |
| Ethyl 2-octenoate | 127.7 | 120 |
| 2,6-Dimethylthiophenol | 84.4 | 85.5 |
| Benzyl alcohol, p,alpha-dimethyl- | 77.2 | 71.8 |
| beta-Ocimene | 111.5 | 92 |
| Benzyl butyrate | 70 | 64.7 |
| Melonal | 52 | 57 |
| 3-Acetyl-2,5-dimethylfuran | 73.5 | 61 |
| Ethyl 2-benzylacetoacetate (Ethyl 2-acetyl-3-phenylpropionate) | 98 | 115 |
| Salicylaldehyde | 66.9 | 65.6 |
| 3-(2-Furyl)acrolein | 68.4 | 66.5 |
| Safranal | 73 | 74.5 |
| 3-Butenyl isothiocyanate | 99.4 | 85.8 |
| Myricitrin | 70.5 | 83.2 |
| Methyl 2-methyl-3-furyl disulfide | 52.6 | 52 |
| 2,4-trans,trans-Undecadienal | 86.4 | 85.4 |
| 2-Chloroacetophenone | 91.4 | 103 |
| 2-Tridecenal | 85.6 | 101 |
| 2,4-Decadienol | 48.6 | 52.2 |
| (2E)-Undecenal | 59.6 | 48.8 |
| alpha-Amylcinnamaldehyde | 86.6 | 82.7 |

TABLE 1(d)

Compounds that activate only A1 and A1V1, with V1 having negative effect on A1V1 activity.
V1 is considered as having negative effect in instances where the A1V1 activity is at least 20-25% lower than A1 value.

| GRAS Compound at 1 mM or 100 µM (*) | A1 | A1V1 |
|---|---|---|
| 2-Ethylbutyric acid | 67.73 | 34.87 |
| Ethyl 5-oxodecanoate | 51.02 | 28.24 |
| p-Cresol | 60.96 | 38.52 |
| 1-Ethylhexyl Tiglate | 50.60 | 31.87 |
| Ethyl vinyl ketone | 79.50 | 40.61 |
| Rhodinol | 116.27 | 78.75 |
| Octyl 2-furoate | 54.33 | 40.60 |
| Cis-3-nonen-1-ol | 55.00 | 41.22 |
| Isobutyl N-methyl anthranilate | 59.73 | 36.7 |
| 1-Phenyl-1,2-prop anedione* | 100.5 | 71.4 |
| 2-Tridecenal* | 76.3 | 43.5 |
| 3-Mercapto-2-butanone* | 68.9 | 53.3 |
| 4-(2-Methyl-3-furylthio)-5-nonanone* | 52.5 | 34.1 |
| (E,E)-2,4-Dodecadienal | 158.8 | 55.4 |
| Isopropyl phenylacetate | 80.2 | 60.9 |
| Methyl 2-nonynoate | 100.7 | 76.1 |
| 2-mercaptopropanoate | 101.5 | 54.3 |
| (E,E)-2,4-Decadienal | 142.3 | 46 |
| Ethyl salicylate | 41 | 28 |
| Linalool | 52.6 | 20 |
| Hexyl nicotinate | 72.9 | 54.4 |
| 1-(2,2,6-Trimethylcyclohex-2-en-1-yl)-1-penten-3-one | 97.3 | 69.7 |

TABLE 1(d)-continued

Compounds that activate only A1 and A1V1, with V1 having negative effect on A1V1 activity.
V1 is considered as having negative effect in instances where the A1V1 activity is at least 20-25% lower than A1 value.

| GRAS Compound at 1 mM or 100 µM (*) | A1 | A1V1 |
|---|---|---|
| 3-Penten-2-one | 64.2 | 35 |
| Acetaldehyde, phenethyl propyl acetal | 86.4 | 62.2 |
| beta-Caryophyllene | 134.2 | 103.8 |
| 3,7-Dimethyl-7-octen-1-ol | 93.7 | 70.7 |
| 2-Hexen-4-one | 53 | 24.5 |
| Bisabolene | 77 | 46.2 |
| 10-Undecenal | 61.8 | 28 |
| 3-(Methylthio)propionaldehyde | 53.8 | 32.4 |
| Furfuryl acetate | 120 | 91.3 |
| Ethyl hydrocinnamate | 72.2 | 50.9 |
| cis-3-Hexenyl isovalerate | 71.7 | 51.6 |
| 3-Hepten-2-one | 82 | 59 |
| trans-2-Hexenyl butyrate | 48.9 | 20 |
| Propyl benzoate | 40.7 | 25.7 |
| Furfurylthiol acetate | 75.5 | 60 |
| Phenoxyethyl isobutyrate | 81 | 53.9 |
| dec-1-en-3-ol | 90 | 69.5 |

TABLE 1(e)

Compounds that activate only A1 and A1V1, with V1 having positive effect on A1V1 activity.
V1 is considered as having positive effect in instances where the A1V1 activity is at least 20-25% higher than A1 value.

| GRAS Compound at 1 mM or 100 µM (*) or at 0.004% for extract (**) | A1 | A1V1 |
|---|---|---|
| Eugenyl isovalerate | 59.69 | 79.29 |
| Benzoin | 26.25 | 61.81 |
| Prenyl thioacetate | 47.27 | 68.99 |
| Alpha Methyl-4-methoxycinnamaldehyde | 67.06 | 85.80 |
| Furan, tetrahydro-2-(3-phenylpropyl)- | 26.00 | 72.09 |
| L-Piperitone | 45 | 68.40 |
| p-Methoxybenzyl butyrate | 34 | 58.97 |
| 3-(Acetylmercapto)hexyl acetate | 22.3 | 52.79 |
| Trans-p-methoxy cinnamaldehyde | 58.79 | 75.99 |
| 2',4'-Dimethylacetophenone | 24.40 | 45.30 |
| L-Menthyl acetate | 44.88 | 60.47 |
| Trans-p-methoxy cinnamaldehyde | 58.40 | 75.99 |
| Hexyl butyrate | 43.2 | 55.89 |
| 4-Methylbenzyl acetate | 58.94 | 88.05 |
| Cinnamomum zeylanicum bark oil** | 50.33 | 65.88 |
| Curcumin* | 102.2 | 150.3 |
| Butyl 4-hydroxybenzoate* | 98.7 | 127.3 |
| 4-Ethoxybenzaldehyde | 62 | 103 |
| Citral dimethyl acetal | 101.6 | 137.2 |
| 6-Methoxyquinoline | 57.8 | 130.5 |
| Cyclamen aldehyde | 94.1 | 120.9 |
| Allyl-alpha-ionone | 52.6 | 89.7 |
| Propane, 1-isothiocyanato-3-(methylthio)- | 81.6 | 114.6 |
| Isopropyl isothiocyanate | 41.8 | 71.6 |
| Isothiocyanic acid 4-penten-1-yl ester | 62.2 | 74.8 |
| 5-Methyl-2-phenyl-2-hexenal | 60.5 | 89.8 |
| 2-Phenylpropyl isobutyrate | 67.4 | 102.3 |
| 3-Methylbutyl isothiocyanate | 61.1 | 111.2 |
| Methyl linoleate | 31 | 81.7 |
| 2-Phenyl-2-butenal | 65.8 | 82.8 |
| 2-Dodecenal | 65.5 | 82.8 |
| p-Menth-8-en-2-one | 39.9 | 59.5 |
| Cinnamaldehyde | 51.2 | 77.3 |
| Sorbic acid methyl ester | 46.4 | 83.3 |

TABLE 1(f)

Compounds that activate only V1 and A1V1, with A1 having no impact on A1V1 activity

| GRAS Compound at 1 mM or at 0.004% for extract | A1V1 | V1 |
|---|---|---|
| Gamma-Undecalactone | 57.8 | 64.1 |
| Epsilon-Decalactone | 52.9 | 47.7 |
| 4-Decanolide | 35.8 | 40.9 |
| 3-Heptyldihydro-5-methylfuran-2(3H)-one | 40.5 | 45.5 |
| Tannins | 69.4 | 52.7 |
| Gamma-Octanolactone | 70.2 | 72.9 |
| 3-(5-Methyl-2-furyl)butanal | 91.6 | 103.4 |
| 2-Furanacrolein, alpha-phenyl- | 66.2 | 55.7 |
| p-tert-Butylphenol | 108.9 | 110.5 |
| Indole | 42.9 | 53.3 |
| Octanoic acid | 83.4 | 73.7 |
| 3-Acetyl-2,5-dimethylthiophene | 84.9 | 95.1 |

TABLE 1(g)

Compounds that activate only V1 and A1V1, with A1 having positive effect on A1V1 activity.
A1 is considered as having positive effect in instances where the A1V1 activity is at least 20-25% higher than V1 value.

| Compound at 1 mM or at 0.004% for extract | A1V1 | V1 |
|---|---|---|
| *Rosmarinus officinalis* essential oils | 50.7 | 37.7 |
| Delta-tetradecalactone | 61.7 | 33.0 |
| Tolylaldehyde glyceryl acetyl | 110.7 | 53.0 |
| Isobutyle acetoacetate | 81.9 | 54.1 |
| Protocatechuic acid | 121.05 | 60.6 |
| Furfuryl methyl sulfide | 111.6 | 50.1 |
| Acetic acid, thio- | 115.1 | 61.9 |
| 6-Pentyl-alpha-pyrone | 95.2 | 66.1 |
| m-Homosalicylaldehyde | 140.7 | 56.5 |
| Adipic acid | 70.4 | 47.6 |
| 5-Nonanone, 4-[(2-methyl-3-furanyl)thio]- | 64 | 40.6 |
| Nonivamide | 135.6 | 91.4 |
| 18beta-Glycyrrhizinic acid | 162.7 | 100.9 |
| 1-Propene, 3,3'-thiobis- | 108.4 | 47.3 |
| alpha-Methylcinnamaldehyde | 104.4 | 54.6 |
| 4-(p-Acetoxyphenyl)-2-butanone | 91.8 | 58.9 |
| 4'-Methylacetophenone | 136.6 | 55 |
| 5-Methyl-2-thiophenecarboxaldehyde | 111.4 | 58.9 |
| 1,3-Dithiolane, 2-methyl- | 119.9 | 66.2 |
| 4-Ethylbenzaldehyde | 120.3 | 56.3 |

TABLE 1(h)

Compounds that activate only V1 and A1V1, with A1 having negative effect on A1V1 activity.
A1 is considered as having negative effect in instances where the A1V1 activity is at least 20-25% lower than V1 value.

| Compound at 1 mM or 100 µM (**) | A1V1 | V1 |
|---|---|---|
| Piperine | 57.1 | 120.1 |
| Gluconic acid, monopotassium salt | 14.0 | 33.0 |
| Tartaric acid | 29.6 | 55.8 |
| L-(+)-Tartaric acid* | 38.4 | 60.4 |
| Anisole* | 34.7 | 48.3 |
| 2,4-Dodecadienal* | 53.5 | 199.1 |
| 2,4-Dodecadienal* | 53.5 | 199.1 |
| 2,5-Dimethylphenol | 34.2 | 81.2 |
| 2,6-Dimethylphenol | 45.8 | 72.1 |
| 2-Isopropylphenol | 83.5 | 108.2 |
| (+)-Neomenthol | 44.8 | 68.8 |
| 3-Methyl-1-phenyl-3-pentanol | 70.5 | 100.5 |

TABLE 1(i)

Compounds that activate only A1, or A1 and V1, but not A1V1. Values less than 20-25% are considered inactive.

| Compound at 1 mM or 100 µM (*) | A1 | A1V1 | V1 |
|---|---|---|---|
| Propylparaben | 93.2 | 2.1 | 1.6 |
| Malic acid | 1.9 | 2.4 | 67.5 |
| 2-Methylbutyl isovalerate | 1.7 | 2.1 | 75.3 |
| 2,4,5-Trimethyl-3-oxazoline* | 2.1 | 4.1 | 100.7 |
| Heptaldehyde* | 4.3 | 2.4 | 65.3 |
| 2-Ethylfuran* | 1.2 | 1.8 | 58.7 |
| Desoxycholic acid* | 3.2 | 2.9 | 84.4 |
| N-Vanillylnonanamide* | 69 | 1.2 | 65.5 |

Among thousands of compounds screened, in the majority of instances the response seen with TRPA1V1 cells is reflective of the response predicted based on what is observed in cells expressing only TRPA1 or TRPV1. Nonetheless, in a surprising number of instances, there is a compound-dependent difference in the response of TRPA1V1, which we hypothesize is due to modulation by TRPA1 and/or TRPV1. Because these key receptors are often co-expressed in the same sensory cells in vivo, an in vitro system which provides stable co-expression of TRPA1 and TRPV1, with formation of hetero-tetramers, provides an advantage in being able to identify extraordinary cases where the results of TRPA1 and TRPV1 studies do not reflect possible interactions between the TRPA1, TRPV1, and TRPA1V1 receptors. These interactions, in a significant number of instances, do not give the predicted, additive result.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application and any patent application or patent to which this application claims priority or benefit thereof, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A method of altering the sensory perception of burning, irritation, or pain from exposure to an oral care composition, the method comprising:
   incorporating a compound that modulates TRPA1V1 activity into an oral care composition;
   wherein the compound is trans,trans-2,4-undecadien-1-al;
   wherein the compound is present in an amount effective to reduce the activation of TRPA1V1 relative to the activation of at least one of TRPA1 or TRPV1.

* * * * *

SEQUENCE LISTING

<160> NUMBER OF SEQ ID NOS: 2

<210> SEQ ID NO 1
<211> LENGTH: 2520
<212> TYPE: DNA
<213> ORGANISM: Homo sapiens

<400> SEQUENCE: 1

| | | | | | |
|---|---|---|---|---|---|
| atgaagaaat | ggagcagcac | agacttgggg | gcagctgcgg | acccactcca | aaaggacacc | 60 |
| tgcccagacc | ccctggatgg | agaccctaac | tccaggccac | ctccagccaa | gccccagctc | 120 |
| tccacggcca | agagccgcac | ccggctcttt | gggaagggtg | actcggagga | ggctttcccg | 180 |
| gtggattgcc | ctcacgagga | aggtgagctg | gactcctgcc | cgaccatcac | agtcagccct | 240 |
| gttatcacca | tccagaggcc | aggagacggc | cccaccggtg | ccaggctgct | gtcccaggac | 300 |
| tctgtcgccg | ccagcaccga | gaagacccte | aggctctatg | atcgcaggag | tatctttgaa | 360 |
| gccgttgctc | agaataactg | ccaggatctg | agagcctgc | tgctcttcct | gcagaagagc | 420 |
| aagaagcacc | tcacagacaa | cgagttcaaa | gaccctgaga | cagggaagac | ctgtctgctg | 480 |
| aaagccatgc | tcaacctgca | cgacggacag | aacaccacca | tcccccctgct | cctggagatc | 540 |
| gcgcggcaaa | cggacagcct | gaaggagctt | gtcaacgcca | gctacacgga | cagctactac | 600 |
| aagggccaga | cagcactgca | catcgccatc | gagagacgca | acatggccct | ggtgaccctc | 660 |
| ctggtggaga | acggagcaga | cgtccaggct | gcggcccatg | gggacttctt | taagaaaacc | 720 |
| aaagggcggc | tggattcta | cttcggtgaa | ctgccctgt | ccctggccgc | gtgcaccaac | 780 |
| cagctgggca | tcgtgaagtt | cctgctgcag | aactcctggc | agacggccga | catcagcgcc | 840 |
| agggactcgg | tgggcaacac | ggtgctgcac | gccctggtgg | aggtggccga | caacacggcc | 900 |
| gacaacacga | gtttgtgac | gagcatgtac | aatgagattc | tgatcctggg | ggccaaactg | 960 |
| cacccgacgc | tgaagctgga | ggagctcacc | aacaagaagg | gaatgatgcc | gctggctctg | 1020 |
| gcagctggga | ccgggaagat | cggggtcttg | gcctatattc | tccagcggga | gatccaggag | 1080 |
| cccgagtgca | ggcacctgtc | caggaagttc | accgagtggg | cctacgggcc | cgtgcactcc | 1140 |
| tcgctgtacg | acctgtcctg | catcgacacc | tgcgagaaga | actcggtgct | ggaggtgatc | 1200 |
| gcctacagca | gcagcgagac | ccctaatcgc | cacgacatgc | tcttggtgga | gccgctgaac | 1260 |
| cgactcctgc | aggacaagtg | ggacagattc | gtcaagcgca | tcttctactt | caacttcctg | 1320 |
| gtctactgcc | tgtacatgat | catcttcacc | atggctgcct | actacaggcc | cgtggatggc | 1380 |
| ttgcctccct | ttaagatgga | aaaaactgga | gactatttcc | gagttactgg | agagatcctg | 1440 |
| tctgtgttag | gaggagtcta | cttcttttc | cgagggattc | agtatttcct | gcagaggcgg | 1500 |
| ccgtcgatga | agaccctgtt | tgtggacagc | tacagtgaga | tgcttttctt | tctgcagtca | 1560 |
| ctgttcatgc | tggccaccgt | ggtgctgtac | ttcagccacc | tcaaggagta | tgtggcttcc | 1620 |
| atggtattct | ccctggcctt | gggctggacc | aacatgctct | actacacccg | cggtttccag | 1680 |
| cagatgggca | tctatgccgt | catgatagag | aagatgatcc | tgagagacct | gtgccgtttc | 1740 |
| atgtttgtct | acatcgtctt | cttgttcggg | ttttccacag | cggtggtgac | gctgattgaa | 1800 |
| gacgggaaga | atgactccct | gccgtctgag | tccacgtcgc | acaggtggcg | ggggcctgcc | 1860 |
| tgcaggcccc | ccgatagctc | ctacaacagc | ctgtactcca | cctgcctgga | gctgttcaag | 1920 |
| ttcaccatcg | gcatgggcga | cctggagttc | actgagaact | atgacttcaa | ggctgtcttc | 1980 |
| atcatcctgc | tgctggccta | tgtaattctc | acctacatcc | tcctgctcaa | catgctcatc | 2040 |
| gccctcatgg | gtgagactgt | caacaagatc | gcacaggaga | gcaagaacat | ctggaagctg | 2100 |

```
cagagagcca tcaccatcct ggacacggag aagagcttcc ttaagtgcat gaggaaggcc    2160
ttccgctcag gcaagctgct gcaggtgggg tacacacctg atggcaagga cgactaccgg    2220
tggtgcttca gggtggacga ggtgaactgg accacctgga acaccaacgt gggcatcatc    2280
aacgaagacc cgggcaactg tgagggcgtc aagcgcaccc tgagcttctc cctgcggtca    2340
agcagagttt caggcagaca ctggaagaac tttgccctgg tccccctttt aagagaggca    2400
agtgctcgag ataggcagtc tgctcagccc gaggaagttt atctgcgaca gttttcaggg    2460
tctctgaagc cagaggacgc tgaggtcttc aagagtcctg ccgcttccgg ggagaagtga    2520
```

<210> SEQ ID NO 2
<211> LENGTH: 3360
<212> TYPE: DNA
<213> ORGANISM: Homo sapiens

<400> SEQUENCE: 2

```
atgaagtgca gcctgaggaa gatgtggcgc cctggagaaa agaaggagcc ccagggcgtt      60
gtctatgagg atgtgccgga cgacacggag gatttcaagg aatcgcttaa ggtggttttt     120
gaaggaagtg catatggatt acaaaacttt aataagcaaa agaaattaaa acatgtgac     180 gatatggaca ccttcttctt gcattatgct gcagcagaag gccaaattga gctaatggag     240
aagatcacca gagattcctc tttggaagtg ctgcatgaaa tggatgatta tggaaatacc     300
cctctgcatt gtgctgtaga aaaaaaccaa attgaaagcg ttaagtttct tctcagcaga     360
ggagcaaacc caaacctccg aaacttcaac atgatggctc ctctccacat agctgtgcag     420
ggcatgaata atgaggtgat gaaggtcttg cttgagcata gaactattga tgttaatttg     480
gaaggagaaa atgaaacac agctgtgatc attgcgtgca ccacaaataa tagcgaagca     540
ttgcagattt tgcttaacaa aggagctaag ccatgtaaat caaataaatg gggatgtttc     600
cctattcacc aagctgcatt ttcaggttcc aaagaatgca tggaaataat actaaggttt     660
ggtgaagagc atgggtacag tagacagttg cacattaact ttatgaataa tgggaaagcc     720 accccctctcc acctggctgt gcaaaatggt gacttggaaa tgatcaaaat gtgcctggac     780
aatggtgcac aaatagaccc agtggagaag ggaaggtgca cagccattca tttttgctgcc     840 acccagggag ccactgagat tgttaaactg atgatatcgt cctattctgg tagcgtggat     900
attgttaaca caaccgatgg atgtcatgag accatgcttc acagagcttc attgtttgat     960
caccatgagc tagcagacta tttaatttca gtgggagcag atattaataa gatcgattct    1020
gaaggacgct ctccacttat attagcaact gcttctgcat cttggaatat tgtaaatttg    1080
ctactctcta aggtgcccca agtagacata aaagataatt ttggacgtaa ttttctgcat    1140
ttaactgtac agcaaccttta tggattaaaa aatctgcgac tgaatttat gcagatgcaa    1200 cagatcaaag agctggtaat ggatgaagac aacgatgggt gtactcctct acattatgca    1260
tgtagacagg gggccctgg ttctgtaaat aacctacttg gctttaatgt gtccattcat    1320
tccaaaagca aagataagaa atcacctctg catttttgcag ccagttatgg gcgtatcaat    1380
acctgtcaga ggctcctaca agacataagt gatacgaggc ttctgaatga aggtgacctt    1440
catggaatga ctcctctcca tctggcagca agaatggaca tgataaagt agttcagctt    1500 cttctgaaaa aggtgcatt gtttctcagt gaccacaatg gctggacagc tttgcatcat    1560
gcgtccatgg gcgggtacac tcagaccatg aaggtcattc ttgatactaa tttgaagtgc    1620
acagatcgct tggatgaaga cgggaacact gcacttcact ttgctgcaag ggaaggccac    1680
```

```
gccaaagccg ttgcgcttct tctgagccac aatgctgaca tagtcctgaa caagcagcag    1740
gcctccttt  tgcaccttgc acttcacaat aagaggaagg aggttgttct tacgatcatc    1800
aggagcaaaa gatgggatga atgtcttaag attttcagtc ataattctcc aggcaataaa    1860
tgtccaatta cagaaatgat agaatacctc cctgaatgca tgaaggtact tttagatttc    1920
tgcatgttgc attccacaga agacaagtcc tgccgagact attatatcga gtataatttc    1980
aaatatcttc aatgtccatt agaattcacc aaaaaaacac ctacacagga tgttatatat    2040
gaaccgctta cagccctcaa cgcaatggta caaataacc  gcatagagct tctcaatcat    2100
cctgtgtgta aagaatattt actcatgaaa tggttggctt atggatttag agctcatatg    2160
atgaatttag gatcttactg tcttggtctc atacctatga ccattctcgt tgtcaatata    2220
aaaccaggaa tggctttcaa ctcaactggc atcatcaatg aaactagtga tcattcagaa    2280
atactagata ccacgaattc atatctaata aaaacttgta tgattttagt gttttttatca   2340
agtatatttg ggtattgcaa agaagcgggg caaattttcc aacagaaaag gaattatttt    2400
atggatataa gcaatgttct tgaatggatt atctacacga cgggcatcat ttttgtgctg    2460
cccttgtttg ttgaaatacc agctcatctg cagtggcaat gtggagcaat tgctgtttac    2520
ttctattgga tgaattcttt attgtatctt caaagatttg aaaattgtgg aatttttatt    2580
gttatgttgg aggtaatttt gaaaactttg ttgaggtcta cagttgtatt tatcttcctt    2640
cttctggctt ttggactcag cttttacatc ctcctgaatt tacaggatcc cttcagctct    2700
ccattgcttt ctataatcca gaccttcagc atgatgctag gagatatcaa ttatcgagag    2760
tccttcctag aaccatatct gagaaatgaa ttggcacatc cagttctgtc ctttgcacaa    2820
cttgtttcct tcacaatatt tgtcccaatt gtcctcatga atttacttat tggtttggca    2880
gttggcgaca ttgctgaggt ccagaaacat gcatcattga agaggatagc tatgcaggtg    2940
gaacttcata ccagcttaga gaagaagctg ccactttggt ttctacgcaa agtggatcag    3000
aaatccacca tcgtgtatcc caacaaaccc agatctggtg ggatgttatt ccatatattc    3060
tgttttttat tttgcactgg ggaaataaga caagaaatac caaatgctga taaatcttta    3120
gaaatggaaa tattaaagca gaaataccgg ctgaaggatc ttacttttct cctggaaaaa    3180
cagcatgagc tcattaaact gatcattcag aagatggaga tcatctctga gacagaggat    3240
gatgatagcc attgttcttt tcaagacagg tttaagaaag agcagatgga acaaaggaat    3300
agcagatgga atactgtgtt gagagcagtc aaggcaaaaa cacaccatct tgagccttag    3360
```